United States Patent [19]

Ballan et al.

[11] Patent Number: 4,981,465
[45] Date of Patent: Jan. 1, 1991

[54] DISPOSABLE CLOSURE MEANS FOR AN ARTIFICIAL OSTOMY OPENING OR AN INCONTINENT NATURAL ANUS

[75] Inventors: Akeel Ballan, Copenhagen; Flemming Burcharth, Herlev; Nils E. Krogh, Rodoure; Frederik Kylberg, Karlstad; Tove Linnemann, Hersholm; Hans Olsen, Bronshoj; Sten N. Rasmussen, Aalborg, all of Denmark

[73] Assignee: Coloplast A/S, Denmark

[21] Appl. No.: 497,830

[22] Filed: Mar. 22, 1990

Related U.S. Application Data

[63] Continuation of Ser. No. 261,233, Oct. 24, 1988, abandoned, which is a continuation of Ser. No. 195,144, May 18, 1988, abandoned, which is a continuation of Ser. No. 817,039, Jan. 8, 1986, abandoned.

[30] Foreign Application Priority Data

Jan. 15, 1985 [DK] Denmark .............................. 187/85

[51] Int. Cl.$^5$ ................................................ A61F 2/02
[52] U.S. Cl. .............................. 600/32; 128/DIG. 25; 128/887
[58] Field of Search ....................... 128/DIG. 25, 887; 604/286, 387, 333; 600/29-32

[56] References Cited

U.S. PATENT DOCUMENTS

| | | | |
|---|---|---|---|
| 1,887,526 | 11/1931 | Spielberg et al. | 604/287 |
| 4,088,132 | 5/1978 | Wood | 128/285 |
| 4,143,423 | 3/1979 | Sternlieb | 2/168 |
| 4,209,009 | 6/1980 | Hennig | . |
| 4,231,369 | 11/1980 | Sorensen et al. | 128/283 |
| 4,258,704 | 3/1981 | Hill | 600/32 |
| 4,365,621 | 12/1982 | Brundin | 128/1 R |
| 4,367,732 | 1/1983 | Poulsen et al. | 128/156 |
| 4,693,236 | 9/1987 | Leprevost | 128/DIG. 25 |

FOREIGN PATENT DOCUMENTS

| | | |
|---|---|---|
| 2363563 | 12/1973 | Fed. Rep. of Germany . |
| 2447682 | 7/1974 | Fed. Rep. of Germany . |
| 2717608 | 4/1977 | Fed. Rep. of Germany . |
| 1471158 | 4/1977 | United Kingdom . |
| 1571382 | 7/1980 | United Kingdom . |

OTHER PUBLICATIONS

Portion of Publication, Polyvinyl Alcohols from the Condensed Chemical Dictionary.

Primary Examiner—Randall L. Green
Assistant Examiner—K. M. Reichle
Attorney, Agent, or Firm—Leydig, Voit & Mayer

[57] ABSTRACT

A disposable closure for an artificial or an incontinent natural intestinal opening has a porous, elastic, air-filled body which in a state not influenced by external compressive forces is a substantially cylindrical, conical or bell-shaped structure having a cross-sectional are, measured halfway between its ends, of at least the double of the cross-sectional area of the intestinal duct for which it is intended. When supplied by the manufacturer, this elastic body is compressed to a substantially cylindrical shape having a cross-sectional area as or slightly below that of the intestinal duct in question. The elastic body is maintained in that compressed state by a moisture- and/or heat sensitive material the shape-maintaining effect of which is rapidly eliminated upon contact with the moisture content of the intestine and/or the heat of the human body. The elastic body may for instance be made of a foam plastic and the shape-maintaining material may for instance be a cover of polyvinyl alcohol.

4 Claims, 2 Drawing Sheets

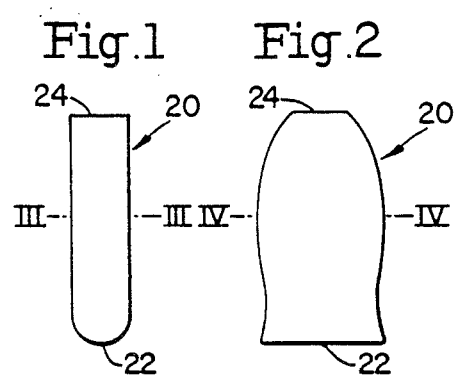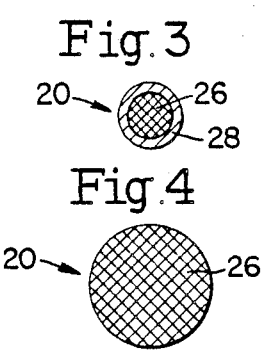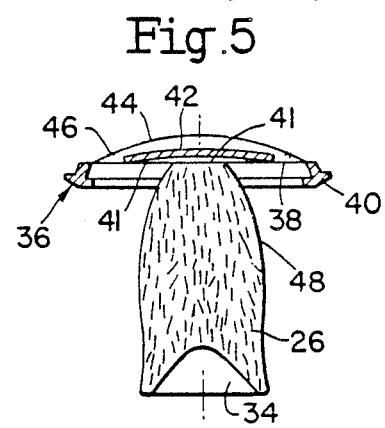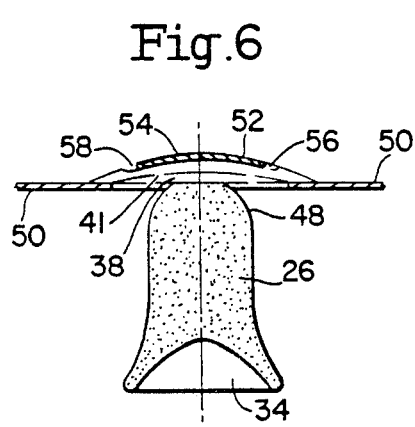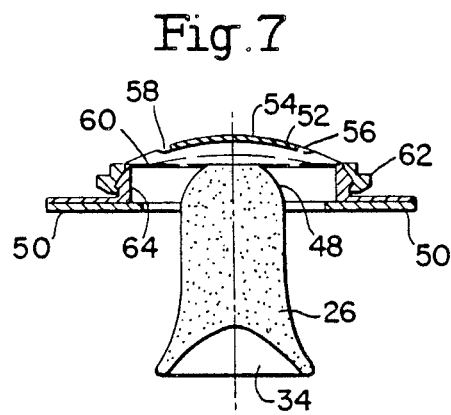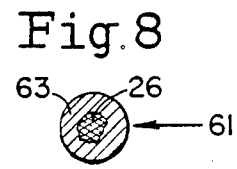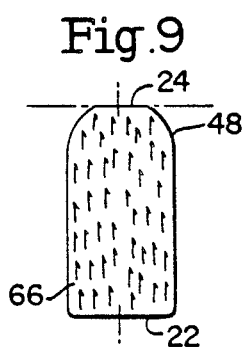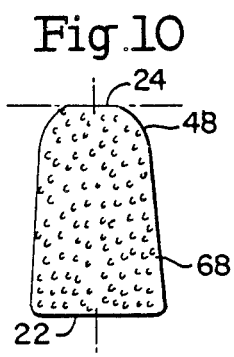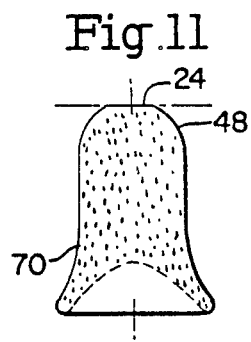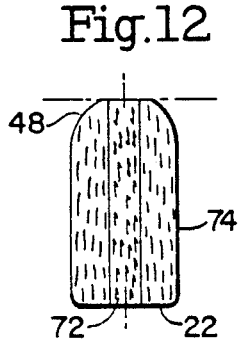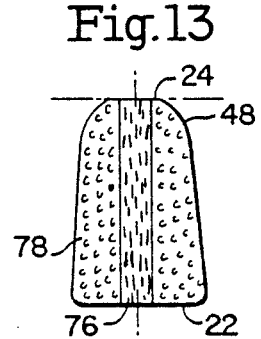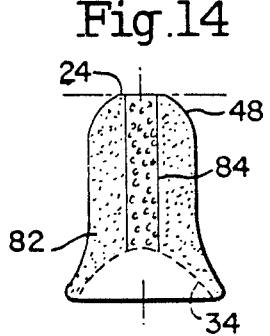

DISPOSABLE CLOSURE MEANS FOR AN ARTIFICIAL OSTOMY OPENING OR AN INCONTINENT NATURAL ANUS

This application is a continuation of application Ser. No. 261,233 filed Oct. 24, 1988 which is a continuation of Ser. No. 195,144 filed May 18, 1988 which is a continuation of Ser. No. 817,039 filed Jan. 8, 1986, all of which are now abandoned.

FIELD OF THE INVENTION

The present invention relates to a disposable closure for an artificial or an incontinent natural intestinal opening, consisting of or containing an elastic, air-filled body. Artificial intestinal openings, i.e. enterostomies such as colostomies and ileostomies, cannot be controlled at will and therefore of necessity are incontinent. Most often the visceral contents therefrom is collected in bags but frequently one prefers a proper closing means for the intestine which in such cases is emptied and possibly rinsed at intervals. Faeces from an incontinent natural anal opening sometimes is collected by means of diaper-like appliances but that is unpleasant and it is therefore usually preferred to close an incontinent anus with a proper closure or plug.

TECHNICAL BACKGROUND

From German patent specification Nos. 2 363 563 and its addition 2 447 682 as well as corresponding other specifications, e.g. GB No. 1 471 158, it is known to close artificial intestinal openings with a magnetic plug held by a ring magnet surgically implanted around the portion of the intestine adjacent the surface of the body. The tightening against unintended discharge of intestinal contents is ensured between a plate-shaped part of the plug and the skin, which necessitates a rather strong magnet action which in many cases is uncomfortable and in adverse cases may cause some tissue necrotization. Closures of this type are not suitable for very fat patients, for patients having varying weight and for patients in which the outer part of the intestine is oblique relative the skin surface because in these cases there are big difficulties in rendering the closure tight.

Another type of closure has therefore been developed, viz. a closing plug of a suitable soft, possibly weakly elastic material to be inserted into the part of the intestinal duct in question adjacent the body surface. An example of such a closure is known from German OL No. 27 17 608 and consists of a magnet or surrounded by a tampon-like material which is expansible by the insertion into the intestinal duct or the anus, i.e. meant for both an incontinent natural anus and for ostomies. As the expansible material materials are proposed which expand under the influence of heat or moisture, e.g. cellulosic materials of largely the same kinds as those used in catamenial tampons. The core of magnetic material or the magnet cooperates with a ring magnet implanted in the tissue surrounding the outer of the intestine. An analogous closure without magnetic holding means described in U.S. Pat. No. 4,209,009 according to which a closing tampon for an incontinent natural or an artificial intestinal opening consists of an elongated, substantially cylindrical body of a cellular material being non-homogenous in the longitudinal direction, viz. formed of longitudinally aligned parts having different radial expansion properties when wetted, a first and a third section having high expansion characteristics when wetted and being separated by an intermediate section having lesser expansion characteristics when wetted. A holding ring of non expanding material is surgically implanted around the intestinal opening, and in use the second section of the tampon is situated within this ring.

A further representative of this type of closure means is described in German OL No. 27 17 607. It has similar magnetic holding means as the closure according to DE No. 27 17 608 but the magnetic core is surrounded by a soft elastic, radially compressible material such as a foam plastic and that material is the proper closure means.

None of these more or less tampon-like materials have gained a use worth while mentioning. This is supposed first and foremost to be due to the fact that the proper principle of closing depends upon the absorption of liquid into cellulosic material or foam material of fundamentally the same kind as is used in catamenial tampons, and that the absorption of liquid in these is not always so rapid as to avoid leakage in the first time after the insertion. The pressure against the intestinal wall is low and the tightening consequently often unsatisfactory. In cases where the tampons before the insertion have so large a diameter that the tightening actually is obtained because of the shape of the tampon, the insertion as a rule will be difficult because a compression has to take place, and this may be accompanied by discomfort or pain and risk of damaging the intestinal wall because the surface of the tampons is not smooth.

A closure means of which the tightening effect depends upon absorption of liquid into a largely unelastic material moreover is not very suitable for intestinal closures where a pressure behind it, caused i.a. by intestinal gas, will tend to expel the closure or allow not only intestinal gas but also other contents of the intestine to bypass the closure means, between that and the intestinal wall.

BRIEF DESCRIPTION OF THE INVENTION

It is the object of the invention to provide a disposable closure for intestinal openings that does not have the drawbacks of the known closures and which may be easily inserted into an intestine without the risk of mechanical damage to the intestinal wall and which rapidly thereafter assumes a state in which it tightens satisfactorily against outflow of intestinal contents at the wrong moment.

This is obtained if according to the invention the elastic, air-filled body in a state not influenced by external compressive forces is a substantially cylindrical, conical or bell-shaped structure having a cross-sectional area, measured halfway between its ends, of at least the double of the cross-sectional area of an intestinal opening to which it is adapted, said elastic body being radially compressed to a substantially cylindrical shape having a cross-sectional area as or slightly below that of the intestinal opening to which it is adapted, the elastic body being maintained in that state by a moisture- and/or heat-sensitive material the shape-maintaining effect of which is rapidly eliminated upon contact with the moisture content of the intestine and/or the human body heat.

It is hereby obtained that the closure before insertion has a sectional shape and size such that it can be easily inserted especially into an ostomy but even into an incontinent anus without causing damage to the intestinal wall and the intestinal mucous membrane. As the diameter of ostomies are rather varying the closure in practice will be manufactured in a series of different sizes, e.g. with diameters in the compressed state from 5 mm up to 20 mm, at intervals of, e.g., 2–3 mm. Closures according to the invention with diameters in the compressed state of 8, 10, 12 and 14 mm, respectively, will together correspond to the need of more than 90% of the users. It goes without saying that the closure in the "natural" state uninfluenced by compressive forces must also be suitable for various sizes of the outer part of the intestinal duct in question.

Though the shape of the closure in the compressed state is largely cylindrical, it may be weakly conical with the smaller diameter in the proximal end, or bevelled in that end. The proximal end of the closure is the end which after insertion into an ostomy or anus is closest to the centre of the human body, whereas the distal end is that adjacent the surface of the human body.

Before the insertion the closure should only be compressed in the radial direction, not in the axial direction. Its length will typically be 3–6 cm.

DESCRIPTION OF VARIOUS EMBODIMENTS OF THE INVENTION

When the material maintaining the closure in the compressed state is exposed to the moisture always present in the intestine and the body heat, its shape maintaining effect is rapidly eliminated, which causes the closure to attempt at assuming its natural size and shape, i.e. a state wherein it is not influenced by the centripetally acting forces of the moisture and/or heat sensitive material. However, the intestinal wall will prevent the closure from assuming its full natural size since in the fully expanded state it must have at least the double sectional area compared to that of the compressed state, whereby the elasticity of the closure body presses it against the intestinal wall so as to cause a tightening effect. The pressure at which the closure in its non-compressed state may be compressed in the radial direction according to the invention should not substantially exceed the vein pressure which is normally between 15 and 25 $P/cm^2$.

Various combinations of materials permit the closure to be compressed as described prior to use and yet to assume rapidly after insertion into the intestine the expanded state causing the tightening. According to the invention the closure thus at least partially may consist of a body of an elastic, porous, air-filled, water-insoluble material compressed to the cylindrical state with a cross-sectional area as or slightly below that of the outer part of the intestinal duct into which it is to be inserted, the compression being caused by a thin cover of a material which is rapidly dissolved or disintegrated by the moisture of the intestine and/or the body heat so as to inactivate the centripetal shape-maintaining effect. This represents a particularly simple manner of ensuring that the closure rapidly expands to a tightening state after the insertion into the intestine but yet has so small diameter before insertion that the insertion does not cause discomfort or injures the intestinal wall.

This, however, should not exclude the use of a hydrophilic material which secondarily, apart from the rapid expansion caused by the elasticity after the elimination of the shape-maintaining effect, contributes to the tightening by virtue of a swelling owing to the effect of moisture. An example of such a material is described in U.S. Pat. No. 3,903,232.

The porous, elastic, water-insoluble, air-filled body according to the invention advantageously may consist in its entirety of a relatively soft, open-cell, elastic polymer foam, preferably an open-cell polyurethane foam. As a rule it will be hydrophilic but it may be hydrophobic.

The elastic, porous, air-filled, water-insoluble body may be prepared from an open-cell, hydrophilic polyurethane foam which in addition to its elasticity is swellable in the intestinal fluid so as to increase the tightening effect of the closure.

Even other foam polymers having an elastic nature, e.g. a silicone foam or a foam of polyvinyl chloride (PVC), may come into consideration as well as foam rubber. The pore size should not be too big since thereby seeping through the material is risked in cases of using the closure for ileostomies because the content of the small intestine contains much more water than the content of the large intestine and the rectum. An expedient average pore diameter suitable for most situations will be 0.2 mm.

The porous, air-filled, water-insoluble body encased by the cover according to the invention may also consist of a polymer foam having closed cells and be provided with a longitudinal channel (axial or eccentrical or possibly obliquel relative the axis) extending from one end of said body to the other and consisting of a water-insoluble material passable for gaseous substances and being in the form of fibres of native or modified cellulose or of an open-cell polymer foam. The channel allows the passage of intestinal gas, at least in the first time after the closure has been inserted into the intestine but may possibly later serve at absorbing liquid from the intestine, especially in case of an ileostomy. If the channel is of a markedly hydrophobic material and has appropriately small pores, e.g. pores not exceeding 0.2 mm, liquid cannot normally penetrate into the channel which consequently permanently is available as a gas passage channel.

According to the invention the porous, air-filled, water-insoluble, elastic body may also consist of a three-dimensional network of elastic fibres, preferably thermoplastic polyurethane or thermoplastic rubber fibres. According to the invention the fibres or filaments may be adhesively joined or melt-joined at a large number—but not necessarily all—points of intersection. In this manner there is formed a particularly elastically compressible matrix that can retain the elasticity for a long period of time, even at storing in the compressed state the closure must have when delivered from the manufacturer. Spot welding may for instance be obtained in comparatively low melting fibres by irradiation with a suitable high frequency thermal radiation. The fibres may conveniently be prepared from a thermoplastic rubber but when they are interconnected as mentioned they may also consist of other suitably firm elastomers.

The cover or outer layer according to the invention may consist of a substantially unelastic, substantially water-soluble film material, preferably a film of polyvinyl alcohol. Its thickness may for instance be 0.05–0.2 mm, conveniently about 0.1 mm.

Polyvinyl alcohol (PVAL) is prepared from various polyvinyl acetates by the exchange by alcoholysis of the acetate group wholly or in part with hydroxy groups. At a degree of alcoholysis of 87–89% the PVAL is fully soluble in cold water. Various PVAL films are commercially available, e.g. under the registered trade marks "VINOL"™, "MOWIOL"™ and "POLYVIOL"™.

The cover may also be prepared from a hydrocolloid in sheet or film form, e.g. of alginates, sodium carboxymethylcellulose or gelatine. Other suitable materials for the cover are polyvinylpyrrolidone (PVP) and methyl hydroxypropylcellulose (MHPC).

The cover, which may be placed on the elastic body by a casting process, instead of a material disintegrable by water, may consist of a heat-sensitive material, preferably one that melts at least partially at a temperature below the normal human body temperature. An example of a suitable material of this kind is a film of a polyethylene glycol (PEG) having a suitable thickness and a melting point appropriate to the purpose. It has been found that PEG 1000 (polyethylene glycol of an average molecular weight of about 1000) is suitable as such a material; the melting point is about 35° C. Advantageously one may use a mixture of two or more polyethylene glycols with each its average molecular weight and hence each its softening point or melting point. An expedient cover of this kind consists of about 75% PEG 1000 and about 25% PEG 3000. The latter has a melting point of about 50° C. but the combined product does not have an arithmetical mean of the melting points of the individual components and said material exhibits beginning melting at about 35° C.

According to the invention the cover may also consist of a woven, knit or non-woven textile material or a net of fibres of a plastic material (polymer) which are water-soluble or are swellable in intestinal fluid to a lengthening of at least 100%, preferably at least 200%. In particular if such a cover has the nature of a comparatively wide-meshed net the fibres or filaments should be unelastic or at most elastic to a low degree. They may for instance consist of PVAL but may, e.g. even consist of a markedly hydrophilic material which is highly swellable in water such as a highly hydrophilic cellulose derivative, e.g. carboxymethylcellulose, especially in the form of its sodium salt.

According to the invention it is expedient if the elastic body has been powdered under the cover with a hydrocolloid. When the hydrocolloid immediately upon the disintegration of the cover—and before if the cover is a net—comes into contact with the moisture in the intestine, the hydrocolloid will absorb water and thereby form a slimy layer between the surface of the body and the intestinal wall, the latter being thereby protected against irritation.

A large number of well known substances may be used as the hydrocolloid, e.g. gum guar, gum karaya, hydroxypropylcellulose or algin (the sodium salt of alginic acid) and other alginates, e.g. various mixed Ca, Mg and K salts of alginic acid and alginic acid esters as propyleneglycol alginate. According to the invention it is especially preferred to use sodium carboxymethylcellulose (Na—CMC) which is frequently employed in the food and drug industry and is available in suitable grades, even very pure ones.

When the elastic body compressed and encased in the cover has been powdered with a hydrocolloid, which will normally be fairly fine-grained, it may be expedient if the pores of a thin outer layer of this elastic body are completely or partially closed, the closing being preferably formed as a casting skin. It is hereby avoided that the hydrocolloid powder before swelling runs into the pores of the body; though sooner or later it would swell here and become slimy, there would be no guarantee for the formation of a coherent layer of slime on the surface of the body.

Instead of scattering the two desired properties—the ability of expanding under the influence of the body heat or the intestinal moisture on one hand and the "confinement" in the compressed state—between two distinct members, viz. The elastic body and the cover, according to the invention it is possible to construct the closure in such a manner that it is an elastic, porous body of a cellular or fibrous material of which an outer zone has been impregnated with a material sensitive to moisture and/or heat, said material exerting an adhesive effect maintaining the closure in the compressed state until the moisture of the intestine and/or the body heat eliminates the shape-maintaining adhesive effect.

The basis material in such a closure may be a polyurethane foam as described hereinbefore, or it may be a three-dimensional network of fibres as also described, optionally which adhesive or welding joints in a large number of intersections. An outer layer is impregnated with a material exerting the adhering effect. Such a material may particularly expediently be a hydrocolloid of one of the types mentioned above. A further hydrocolloid particularly suitable as adhesive in this embodiment is gum arabic. In practice one produces such a body by powdering the foam or fibre body with the hydrocolloid in powder form, possibly such that some powder penetrates into the outer layer of the foam, whereupon the powdered body is moistened, preferably with a mist of fine water droplets. Hereby the hydrocolloid powder will penetrate into the foam body, which should have rather fine pores, and when this has taken place the body is compressed to the cylindrical shape or weakly conical shape it must have when supplied by the manufacturer, and is thereafter dried. The hydrocolloid hereby forms a coherent network maintaining the closure body in the shape it had when being dried, but when it comes into contact with moisture in the intestine the adhesive effect will end and the body will expand.

In the uncompressed state the closure, i.e. the foam body or fibrous body may be fully or approximately cylindrical or optionally prismatic with 6 or more lateral faces. Very conveniently the closure in a state uninfluenced by compression forces is substantially conical or bell-shaped having the largest diameter in the proximal end. There is hereby obtained some resistance against the closure being pressed out of the intestine by a pressure behind it, which pressure may in part be due to intestinal gas.

Although a solid of revolution is aimed at with the expressions conical shape or bell-shape, the uncompressed body may also be angular, e.g. 6-, 8- or 12-gonal. The proximal end face of the closure may expediently be concave, which improves the tightening effect because the innermost parts of the closure body are thereby particularly efficiently pressed against the intestinal wall.

Even in the embodiments in which it is not positively stated, the closure body may be provided with a through going axial channel for the escape of intestinal gas. Such a channel may for instance be made of a hydrophobic, open-cell plastic foam having small cells or of a hydrophobic fibrous material and may optionally contain a material, typically activated carbon, for deodorizing the intestinal gas. It is not absolutely necessary that the closure has such a channel if the pressure exerted on the intestinal wall does not substantially exceed the abovementioned vein pressure since in that case the intestinal gas may pass between the closure and the intestinal wall when the gas pressure becomes sufficiently high.

Since even a relatively weak pressure in the intestine will tend to press the closure out of the intestine, it is in practice necessary to supplement the tightening effect exerted by the closure as described by some attachment means.

In its simplest form it merely consists of an adhesive tape attached to the skin around the intestinal opening and bridging it. To avoid the building up of an unpleasantly high pressure in the intestine behind the closure the tape is preferably a microporous tape, e.g. of the kind described in U.S. Pat. No. 3,870,593. If the closure is such that intestinal gas bypasses it, or it has no filter, the microporous tape may be combined with a deodorizing filter of any suitable known type.

Advantageously the closure may be provided in the distal end with a means for direct or indirect attachment to the skin of the user and being supplied with one or more openings for the discharge of intestinal gas; if this is the case, the porous closure body according to the invention may expediently have a constricted neck at which it is provided with the attaching means, which may for instance be a plate, so that the cross-sectional area at this place in the expanded state is at most the same as in the compressed state before being brought into use. Hereby the closure becomes supple and flexible and especially it is avoided that the closure presses against the intestinal wall just at its outer end, adjacent the skin.

The means for direct or indirect attachment to the skin may be provided with a coupling ring adapted to sealing engagement with another coupling ring connected to a skin barrier adapted to adhesive attachment to the skin. Any suitable known coupling rings may be used. The skin barrier very conveniently is of the kinds described in the U.S. Pat. Nos. 4,231,369 and 4,367,732.

The closure may if desired be provided with a string for use at its removal from the intestine.

BRIEF DESCRIPTION OF THE DRAWINGS

In the following the closure according to the invention will be described more fully with reference to the drawings which shows some embodiments thereof In the drawings FIG. 1 shows a lateral view of a closure according to the invention in the compressed state before insertion into an intestine, FIG. 2 the same in lateral view of the closure in its natural state not influenced by compression forces, FIG. 3 a cross-section of the same in the compressed state, along line III—III in FIG. 1, FIG. 4 a cross-section of the same in the natural state, along line IV—IV in FIG. 2, FIG. 5 a longitudinal section of a similar embodiment as that of FIGS. 1-4 in the natural state, yet provided with a means for the attachment of the closure to a skin barrier, FIGS. 6 and 7 similar sections, but of closures with different attachment means, FIG. 8 a cross-section of another embodiment in the compressed state, FIGS. 9-14 schematic longitudinal sections of various further embodiments (with no attachment means shown) in the natural state, FIG. 15 a schematic section of the abdominal wall of a user just after a closure as shown in FIG. 1 has been inserted into an ostomy, FIG. 16 a similar section after the fixation of the closure in the compressed state has been released, and FIG. 17 a similar view at a later moment at which the intestine has been filled.

DETAILED DESCRIPTION OF THE DRAWINGS

Figure 15:
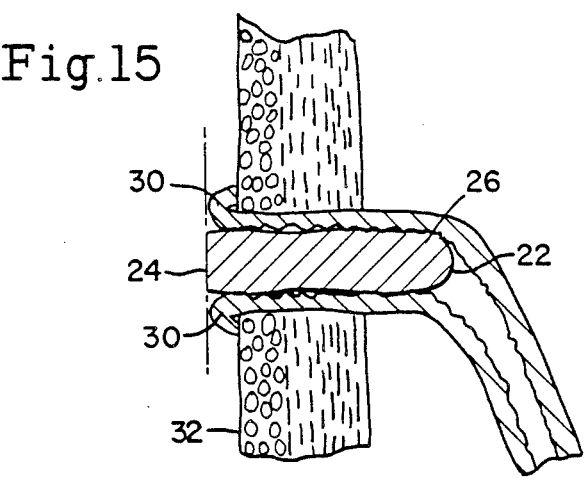
FIGS. 15-17 are in approximately the natural size of the closure whereas the other Figures have been reduced by about 15% linearly.

An intestinal closure 20 shown in FIGS. 1-4 and 15-17 in the compressed state shown in FIGS. 1, 3 and 15 is a cylindrical body weakly tapering in the proximal end 22. It is observed that the embodiment shown is intended for a comparatively narrow intestine, and for intestines having a larger diameter the closure has a bigger cross-sectional area than shown in FIGS. 1-4, both in the compressed and expanded states.

Figure 16:
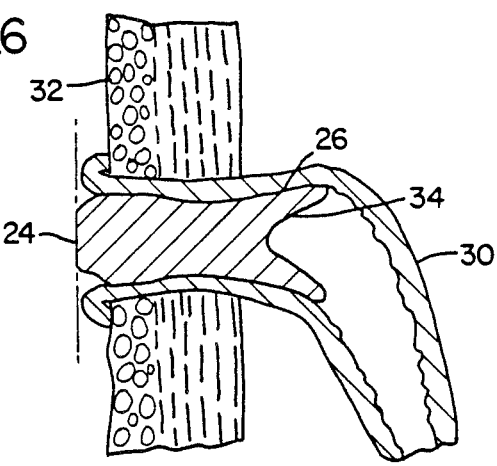
Figure 17:
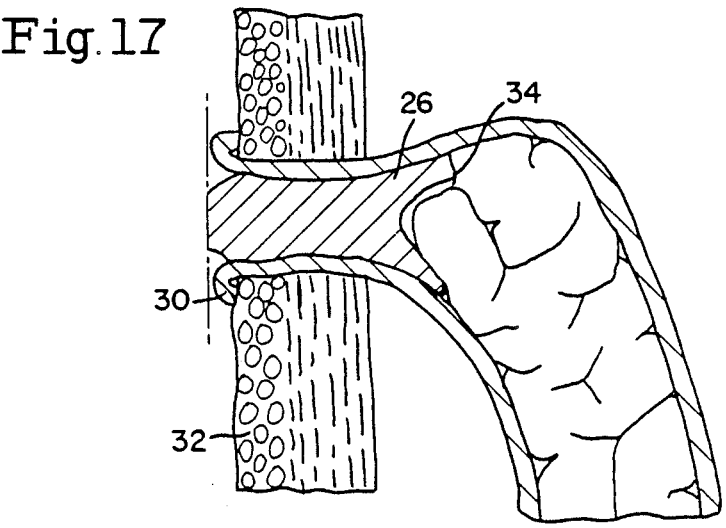

The closure 20 consists of a body 26 of a soft, elastic, water-insoluble material, notably an open-cell polymer foam which in the state shown in FIGS. 1 and 3 has been compressed radially to about the half of the cross-sectional area it has in its free state not influenced by centripetally acting compression forces, and it is held in that state by a thin cover or wrapping 28 of a material that is disintegrable by water and intestinal fluid, preferably a thin film of PVAL; it is observed that the thickness of the cover is highly exaggerated in FIG. 3. Soon after the insertion into an ostomy or the natural rectum the cover 28 will become disintegrated, viz. Dissolved, whereby the porous material expands to a size limited by the intestinal wall as is seen in FIGS. 16-17; FIGS. 2 and 4 show the diameter of the closure in the expanded (natural), unloaded state.

FIGS. 2 and 16-17 show that the closure in the expanded state is constricted at the distal end; hereby a too high pressure on the intestinal wall 30 is avoided in the area adjacent the skin 32 of the patient. The constriction may be brought about during the manufacture of the body 26, which may be prepared by foaming, e.g., a polyurethane in a mold or by cutting from a bigger block.

Under radial compression of the body 26 the cover 28 may be placed on it, e.g. by wrapping with PVAL film in a single layer with a small overlapping at which the PVAL film adheres to itself by a modest moistening. The mounting may also take place by slipping a tubular film over the body 26.

It is seen from FIGS. 1-4 and 15-17 that the body 26 has only been compressed in the radial direction whereas in the axial direction it has largely the same length in the compressed and the expanded states. Yet in the proximal end it has expediently in the expanded state a concavity 34; it will improve the tightening effect of the closure as the intestine is filled as is seen from FIG. 17 since the intestinal content will tend to distend the edge of the concavity 34.

The closure shown in FIGS. 1-4 and 15-17 can be held within the intestine by means of a porous tape adhesively attached to the skin around the intestinal opening and preferably provided with a deodorizing filter. Such attachment is particularly important if the body 26 has been powdered with a hydrocolloid powder, e.g. Na—CMC; this under the influence of moisture in the intestine forms a slime layer that decreases the friction between the closure and the intestinal wall so that the closure may be easily expelled from the intestine under the influence of the intestinal gas pressure.

The embodiments described in the following may also be provided with a hydrocolloid powder; it will not be discussed in connection therewith.

Except for FIG. 8 the following embodiments are shown in the natural (expanded) state; except for holding means they have in the compressed state largely the same appearance as shown in FIGS. 1, 3 and 15.

The intestinal closure shown in FIG. 5 as that shown in FIGS. 1–4 has a closing body 26 of a soft, open cell polymer foam, preferably polyurethane. Compressed from the state shown in FIG. 5 it is encased in a cover of a film, net or textile material which is disintegrable by the intestinal moisture or body heat. The body 26 is connected to a member 36 attaching the intestinal closure to the skin of the user around the intestinal opening.

The plate 36 contains a lower sheet 38 which at its periphery is connected to coupling means 40 adapted to be pressed into corresponding coupling means in a ring (not shown) which by the aid of a suitable adhesive is attached to the skin around the ostomy. In the lower sheet 38 one or more gas passage openings 41 are provided, allowing an overpressure of intestinal gas to escape. One or more of the openings are situated in the area where body 26 is connected to lower sheet 38, the connection being an annular adhesive bonding or welding. This opening allows a passage of gas through the plastic foam and out via the lower sheet. Above the lower sheet 38 an intermediate sheet 42 is secured in a gas-tight manner and the intermediate sheet 42 has a filter normally consisting of activated carbon. The filter is situated so as to bridge an opening in the intermediate sheet and is partially blocked in a manner such that gases passing the opening in the intermediate sheet must traverse a comparatively long path through the filter. Above the intermediate sheet there is secured a sheet 44 which for aesthetic reasons may be skin-colored. The upper sheet 44 too is provided with passage openings 46, allowing filtered gas to escape.

In the proximal end the expanded closing body 26 for the reason given above has a concavity 34 and it is seen that in the distal end it has a narrower neck portion 48 via which it is attached to plate 36. The constriction to form the neck portion 48 may have been made by shaping before compression as explained in connection with FIGS. 1–4 but it may also have been caused thereby that body 26 in the compressed state has been attached to plate 36, e.g. by gluing or hot melting; in that case the neck portion 48 because of the connection to plate 36 will expand to a lesser degree than the other portions of body 26.

The closure shown in FIG. 6 in the expanded state shown has a closing body 26 with a constricted neck portion 48 and a concavity 34 in the proximal end. Neck portion is connected to an annular skin barrier 50, preferably of the kind described in the U.S. patents mentioned hereinbefore; by means of its adhesive effect the closure may be attached to the skin of the patient around the ostomy or anus without risk of being expelled under the influence of pressure from intestinal gas or solid or liquid intestinal contents. As in FIG. 5 there is a lower sheet secured to the neck portion 48 and in its peripheral part adhesively bonded or heat-sealed to the skin barrier 50. In FIG. 6 the skin barrier is showed as being flat but by a suitable alteration of the shape with regard to the anatomy around anus it may be adapted for closing an incontinent natural anus. The lower sheet has perforations 41 for the passage of intestinal gas. Over the lower sheet 38 a special deodorizing filter 52 has been placed. It consists of two layers of liquid- and gas-tight plastic film between which the filter 54 proper of activated carbon textile material has been placed, with the faces adhesively bonded or heat-sealed to the plastic films. At one end there is an opening 56 in the film facing the skin barrier 50, at the other end an opening 58 in the film facing the outer world. The intestinal gas is forced by its own pressure outwardly through opening 56, through the entire length of activated carbon textile filter 54 and leaves the filter in deodorized state through opening 58.

The closure shown in FIG. 7 has a similar construction but the attachment arrangement to the skin is different. The neck portion 48 of closing body 26 by means of a comparatively rigid plastic material is attached to a coupling ring 62. This coupling ring can be pressed around (and be released from) another coupling ring 64. Ring 64 by adhesive bonding, heat welding or in an other manner is firmly connected with a skin barrier 50 Plate 60 has perforations for the escape of intestinal gas and this is deodorized through a filter 52 of the same kind as in FIG. 6.

FIG. 8 shows a cross-section through an unexpanded closure 61 of another construction than the foregoing ones. This closure does not have any cover of material that can be disintegrated by the water content of the intestine or the body. As the embodiments described it consists of a body 26 of soft, elastic plastic foam. An outer zone 63 has been impregnated with a hydrocolloid, e.g. gum arabic or Na—CMC; the impregnation has been made in the wet condition and the body with the hydrocolloid has thereupon been dried in the compressed state. In principle the impregnation zone may extend through the entire closing body 26 but to obtain a rapid expansion after the insertion into the intestine it is only present in the outer zone 63 which upon an uneven impregnation (which does not necessarily do any harm) may have an irregular contour as intimated in FIG. 8. When the closure 61 is inserted into the intestine the hydrocolloid is dissolved by the intestinal fluid whereby the closing body 26 expands. This type of closure is best suited for the so called wet ostomies, i.e. ileostomies.

FIGS. 9–14 very schematically show longitudinal sections of various intestinal closures in the natural state. They may all be provided with holding means as described with reference to FIGS. 5–7 or be adapted to be held by porous tape and they may all be constructed either with a disintegrable cover or impregnated with a water-soluble hydrocolloid.

All of the closures according to FIGS. 9–14 have a constricted neck portion 48 in the distal end. The closures according to FIGS. 9 and 12 apart from the neck portion are cylindrical with a plane proximal end face 22. The closures according to FIGS. 10 and 13 are conical with the larger diameter in the proximal end 22, which is plane. The closures according to FIGS. 11 and 14 are bell shaped with concave end faces 34.

The closure according to FIG. 9 has a closing body 66 of a three-dimensional network of fibres prepared from a thermoplastic polyurethane or a thermoplastic rubber (block copolymer).

The closure according to FIG. 10 has a closing body 68 of an open-cell silicone foam.

The closure according to FIG. 11 has a closing body 70 of an open-cell polyurethane foam, e.g. "Hypol 2002".

The closure according to FIG. 12 has a core 72 of a fibrous material that particularly well permits the passage of intestinal gas, and an outer layer 74, preferably of another fibrous material The core 72 may expediently be hydrophobic, which reduces or eliminates the possibility of absorption of liquid therein, whereas the outer layer 74 may well be hydrophilic or even swellable in water.

The closure according to FIG. 13 has a fibrous core 76 of a similar nature as the fibrous core 72, and an outer layer 78 of foam plastic, very advantageously polyurethane.

The closure according to FIG. 14 has a core 84 of an open-cell foam plastic allowing passage of gas and may optionally be hydrophobic, and an outer layer 82 also of a foam plastic The latter foam plastic may have open or closed cells.

We claim:

1. A disposable sealing and gas filtering device for incontinent openings of intestinal ducts including ostomy openings surrounded by an annular skin barrier, comprising in combination:
    an elastic body of open-cell polymer foam having first and second ends and capable of rapid radial expansion to seal an incontinent opening, where said first end of said body in the expanded state has a smaller cross-sectional area than the second end and said first end is adapted to be situated adjacent the outer end of the incontinent opening;
    a film cover disintergratable by the influence of temperature and moisture prevailing in an intestinal duct, said film cover compressing said elastic body radially over its entire length to a substantially cylindrical shape having a cross-sectional area about half of the cross-sectional area it possesses in its uncompressed state, said elastic body being dimensioned to fit into the intestinal duct to be sealed;
    a first coupling ring bondable to the annular skin barrier, said first coupling ring having a central opening and a first element of a cooperating connecting member;
    a second coupling ring having a central opening corresponding to the central opening of said first coupling ring, said second coupling ring including a second element of the cooperating connecting member, where combining said first and second elements establishes said coo operating connecting member and establishes a removably attachable gas-tight connection between said first coupling ring and said second coupling ring;
    a first sheet affixed to said second coupling ring within the central opening, said first sheet being affixed to said elastic body, and having one perforation for the passage of intestinal gases;
    a second sheet covering said first sheet in a gas-tight manner and connected at its periphery to said second coupling ring so as to form a space between said first and second sheets, said second sheet being provided with at least one opening for the escape of gases, and
    a filter means being located in said space an being secured to at least one of said first and second sheets.

2. A disposable sealing and gas filtering device, according to claim 1 where said open-cell polymer foam comprises polyurethane.

3. A disposable sealing and gas-filtering device for incontinent natural intestinal openings and ostomy openings surrounded by an annular skin barrier, comprising in combination:
    an elastic body of open-cell polymer foam, having first and second ends capable of rapid radial expansion to seal natural intestinal openings and ostomy openings, where said first end of said body in the expanded state has a smaller cross-sectional area than the second end and said first end is adapted to be situated adjacent the outer end of the intestinal opening;
    a film cover disintegratable by the influence of temperature and moisture prevailing in an intestinal duct, said film cover compressing said elastic body radially over its entire length to a substantially cylindrical shape having a cross-sectional area of about half of the cross-sectional area it possesses in its uncompressed state, said elastic body being dimensioned to fit into the intestinal duct to be sealed;
    a first sheet connected to said first end of said body and connected at its periphery to the annular skin barrier, said first sheet having at least one perforation for the passage of intestinal gases;
    a second sheet covering said first sheet in a gas-tight manner and connected to the annular skin barrier so as to form a space between said first and second sheets, and said second sheet being provided with at least one opening for escape of gases, and
    a filter located in said space and secured to at least one of said first and second sheets in a manner to allow passage of gases through said perforation, said filter and then said opening.

4. A disposable gas sealing and filtering device according to claim 3 where said open cell polymer foam comprises polyurethane.

* * * * *